(12) United States Patent
Chae et al.

(10) Patent No.: US 10,112,187 B2
(45) Date of Patent: Oct. 30, 2018

(54) HIGH STRENGTH SAPO-34 MICROSPHERE CATALYST, METHOD FOR PREPARING SAME, AND METHOD FOR PREPARING LIGHT OLEFINS USING SAME

(75) Inventors: Ho Jeong Chae, Daejeon (KR); Soon Yong Jeong, Daejeon (KR); Chul Ung Kim, Daejeon (KR); Kwang Eun Jeong, Daejeon (KR); Tae Wan Kim, Busan (KR)

(73) Assignee: KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 0 days.

(21) Appl. No.: 13/502,496

(22) PCT Filed: Oct. 4, 2010

(86) PCT No.: PCT/KR2010/006753
§ 371 (c)(1),
(2), (4) Date: Apr. 17, 2012

(87) PCT Pub. No.: WO2011/049301
PCT Pub. Date: Apr. 28, 2011

(65) Prior Publication Data
US 2012/0203046 A1 Aug. 9, 2012

(30) Foreign Application Priority Data
Oct. 22, 2009 (KR) .......................... 10-2009-0100597

(51) Int. Cl.
| | |
|---|---|
| B01J 35/08 | (2006.01) |
| C07C 1/20 | (2006.01) |
| B01J 27/182 | (2006.01) |
| B01J 29/85 | (2006.01) |
| B01J 37/00 | (2006.01) |
| C10G 3/00 | (2006.01) |
| C10G 11/02 | (2006.01) |
| C10G 11/18 | (2006.01) |

(52) U.S. Cl.
CPC ........... *B01J 29/85* (2013.01); *B01J 37/0045* (2013.01); *C07C 1/20* (2013.01); *C10G 3/00* (2013.01); *C10G 11/02* (2013.01); *C10G 11/18* (2013.01); *B01J 2229/42* (2013.01); *C10G 2400/20* (2013.01)

(58) Field of Classification Search
CPC ........................................................ B01J 29/85
See application file for complete search history.

(56) References Cited

U.S. PATENT DOCUMENTS

| | | | |
|---|---|---|---|
| 4,310,440 A | 1/1982 | Wilson et al. | |
| 4,440,871 A * | 4/1984 | Lok et al. | 502/214 |
| 4,499,327 A | 2/1985 | Kaiser | |
| 4,547,616 A * | 10/1985 | Avidan | C07C 1/20 585/639 |
| 5,126,308 A | 6/1992 | Barger et al. | |
| 5,191,141 A | 3/1993 | Barger et al. | |
| 5,475,182 A | 12/1995 | Janssen | |
| 6,207,872 B1 | 3/2001 | Barger et al. | |
| 6,225,254 B1 | 5/2001 | Janssen et al. | |
| 6,448,460 B2 | 9/2002 | Janssen et al. | |
| 6,514,899 B1 * | 2/2003 | Mertens et al. | 502/214 |
| 7,309,679 B2 | 12/2007 | Karch et al. | |
| 7,547,812 B2 | 6/2009 | Sinkler et al. | |
| 2003/0078159 A1 * | 4/2003 | Mertens | B01J 29/85 502/214 |

(Continued)

FOREIGN PATENT DOCUMENTS

| | | |
|---|---|---|
| KR | 10-2002-0010700 A | 2/2002 |
| KR | 10-2002-0013572 A | 2/2002 |

(Continued)

OTHER PUBLICATIONS

Extended European Search Report Appln. No. 10825126.5-1352 / 2492010 PCT/KR201006753; dated Nov. 4, 2014.

*Primary Examiner* — Douglas B Call
(74) *Attorney, Agent, or Firm* — Ladas & Parry LLP; Loren K. Thompson

(57) ABSTRACT

The present invention relates to a high-strength silicoaluminophasphate-34 (SAPO-34) microsphere catalyst, a method for preparing the same, and a method for preparing light olefins by using the same, and when described in more detail, the present invention relates to a method for preparing a SAPO-34 microsphere catalyst, including: spray drying a mixed slurry including a matrix, a binder, an additive, and the like to a SAPO-34 slurry prepared by a hydrothermal synthesizing method using various organic templates such as tetraethylammonium hydroxide (TEAOH), and the like alone or in mixtures to prepare microspheres, and firing the microspheres, and to a SAPO-34 microsphere catalyst for a circulating-fluidized bed reactor, prepared by the preparation method. The SAPO-34 microsphere catalyst of the present invention has excellent reaction activity while having high strength, and thus is appropriate for use in a circulating-fluidized bed reactor requiring high strength of the catalyst. Further, the SAPO-34 microsphere catalyst has a long life-span and excellent conversion rate of $C_1$ to $C_4$ oxygen-including compounds (oxygenates), and thus is appropriate for use in the preparation of light olefins such as ethylene, propylene, butene, and the like.

16 Claims, No Drawings

(56) References Cited

U.S. PATENT DOCUMENTS

| | | | |
|---|---|---|---|
| 2004/0075525 A1 | 4/2004 | Sippola et al. | |
| 2004/0121902 A1 | 6/2004 | Chang et al. | |
| 2006/0245994 A1* | 11/2006 | Watanabe et al. | 423/305 |
| 2006/0293547 A1* | 12/2006 | Mertens | B01J 29/85 585/639 |
| 2007/0004950 A1* | 1/2007 | Sinkler et al. | 585/639 |
| 2007/0032378 A1* | 2/2007 | Karch et al. | 502/208 |
| 2011/0295050 A1* | 12/2011 | Nesterenko | B01J 29/84 585/641 |

FOREIGN PATENT DOCUMENTS

| | | |
|---|---|---|
| KR | 10-699650 B | 3/2007 |
| KR | 10-699654 B | 3/2007 |
| KR | 10-2008-0014154 A | 2/2008 |
| KR | 10-2008-0031505 A | 4/2008 |
| KR | 10-2009-0028018 A | 3/2009 |
| KR | 10-898127 B | 5/2009 |
| WO | WO 2000/74848 A | 12/2000 |
| WO | 03000413 A1 | 1/2003 |
| WO | 2007019211 A1 | 2/2007 |
| WO | WO 2007019211 A1 * | 2/2007 |
| WO | WO 2010/023288 * | 3/2010 |

* cited by examiner

HIGH STRENGTH SAPO-34 MICROSPHERE CATALYST, METHOD FOR PREPARING SAME, AND METHOD FOR PREPARING LIGHT OLEFINS USING SAME

This application is a 371 of PCT/KR2010/006753 filed on Oct. 4, 2010 published on Apr. 28, 2011 under publication number WO 2011/049301 A which claims priority benefits to Korean Patent Application Number 10-2009-0100597 filed Oct. 22, 2009, the entire disclosure of which is incorporated herein by reference.

TECHNICAL FIELD

The present invention relates to a high-strength SAPO-34 microsphere catalyst prepared by hydrothermally synthesizing a mixed synthetic gel in which a synthetic gel including an aluminum phosphate gel and an organic template; and a silica-dissolving solution including a silica precursor and an organic template are mixed, to prepare a SAPO-34 slurry, spray-drying a mixed slurry including the SAPO-34 slurry, a matrix, a binder, and the like to prepare microspheres, and then firing the microspheres, and to a method for preparing the same. Further, the present invention relates to a method for preparing light olefins such as ethylene, propylene, butene, and the like by using the SAPO-34 microsphere catalyst.

BACKGROUND ART

Silicoaluminophosphate (SAPO) molecular sieves have been used as an absorbent and a catalyst. As a catalyst, the SAPO molecular sieves have been used in the processes of fluidized catalytic cracking, hydrocracking, isomerization, polymerization, conversion of alcohols or ethers, and alkylation of aromatic compounds. In particular, in recent years, along with the advent of high oil prices, methods for using a SAPO molecular sieve in the process of converting alcohols or ethers into light olefins are drawing significant attention.

A SAPO molecular sieve was first synthesized by the Union Carbide Co. [U.S. Pat. Nos. 4,310,440 and 4,440,871]. In particular, the same company published documents on how light olefins ($C_2$ to $C_4$ olefins) are prepared from oxygen-including compounds including methanol by using a SAPO-34 catalyst [U.S. Pat. Nos. 4,440,871 and 4,499,327], and major petroleum companies such as UOP, Exxon Mobil, and the like have developed SAPO-34 molecular sieve catalysts as a catalyst for methanol to olefin (MTO) reaction.

In the methanol-to-olefin (MTO) reaction, as another method of enhancing the activity of the catalyst while increasing the yield of light olefins, aluminophosphate molecular sieves substituted with various metals were published in U.S. Pat. Nos. 5,126,308 and 5,191,141, and silicon, magnesium, cobalt, zinc, iron, nickel, manganese, chromium, or mixed components thereof were used as metal components in the documents. In this case, it was reported that silicon is the most favorably used metal and the activity and durability of the catalyst is excellent when particles having a molecular sieve crystal size of less than 1 μm are present in an amount of 50% and particles having a molecular sieve crystal size of more than 2.0 μm are present in an amount of less than 10%, with respect to the whole system and the content of silicon is limited to 0.005 to 0.05 in terms of molar fraction. Further, U.S. Pat. No. 6,207,872 by the same company is an improvement patent of U.S. Pat. No. 5,126,308. It was reported in the patent document that the yield of light olefins is increased when the molar fraction of molecular components is in a range of 0.02 to 0.08 based on the aluminophsphate molecular sieve substituted with the same metal components and the molecular sieve crystal size is 0.1 μm or more. As described above, it is already known that the reaction performance is improved when the crystal size is small. However, when the crystal size is small, it is disadvantageous in that the preparation yield of catalyst powder through filtration and drying is decreased and as a result, costs of preparing a shaped catalyst from a powdered catalyst are increased.

As a specific method of preparing a SAPO molecular sieve, usually, humed silica, silica sol, and the like are used as a silicon precursor, pseudoboehmite, aluminum isoproox-ide, and the like are used as an aluminum precursor, and phosphoric acid is used as a precursor of phosphor, generally in the SAPO molecular sieve. As an organic templates which is used to form the backbone of the molecular sieve which is the most important, tetraethylammonium hydroxide, morpholine, dipropylamine, isopropylamine, diethanolamine, triethylamine, diethylamine, cyclopentylamine, aminomethyl cyclohexane, piperidine, cyclohexylamine, tri-ethyl hydroxyethylamine, pyridine, and the like are known [Korean Patent No. 699,654 and Korean Patent No. 699,650]. However, when the other organic templates except for tetraethylammonium hydroxide are used alone, the crystallinity is lowered and the crystal size is increased too much, and thus it is disadvantageous in that the reaction activity is relatively decreased. Meanwhile, in Korean Patent No. 989,127, it was suggested that the crystallinity and reactivity of the catalyst may be significantly enhanced by using these templates in mixtures, but what is described above is limited to the preparation of powdered catalysts and is not appropriate for use in a circulating-fluidized bed reactor.

In order to commercialize the light olefin process, it is very important to develop a shaped catalyst having excellent sphericity and high strength while having an appropriate size in a circulating-fluidized bed reactor which may regenerate the catalyst continuously. The circulating-fluidized bed reactor is effective in controlling a constant reaction temperature, and particularly, the reaction heat of the exothermic reaction, compared to a fixed bed reactor and advantageous in that productivity is enhanced by contacting reactants with the catalyst safely and uniformly. However, stress of catalytic materials resulting from the high temperature and flow rate of the circulating-fluidized bed reactor acts so significantly that due to attrition of the catalyst in the circulating-fluidized bed reactor, fine particles are produced, thereby leading to loss of the catalyst. Further, fine particles are released while being incorporated into products, and thus a product separation filter is clogged to hamper the reactor from being operated normally, which is problematic. Therefore, in the development of a SAPO catalyst for preparing light olefins, it is particularly important to develop a microsphere SAPO catalyst having excellent abrasion resistance along with optimization of reactivity.

DETAILED DESCRIPTION OF THE INVENTION

Technical Problem

The present invention has made an effort to solve the problems of the SAPO-34 catalyst in the related technology, and as a result, it is to be understood that if the SAPO-34 slurry having a crystal size of 1 μm or less is used without being dried during the preparation of the SAPO-34 catalyst, a microsphere catalyst having an high strength and an average size of 50 to 100 μm may be prepared while reducing the synthetic loss of the catalyst. Further, an optimum shaping condition for preparing a high-strength SAPO-34 microsphere catalyst was found out in which the crystallinity of the catalyst may be significantly enhanced while using organic templates in mixtures, and that may have high reaction activity and long life-span was found even in a circulating-fluidized bed reactor used in the preparation of light olefins, thereby completing the present invention.

Therefore, the present invention provides a SAPO-34 microsphere catalyst, a method for preparing the same, and a method for preparing light olefins using the same.

Technical Solution

In order to solve the above-described problems, an object of the present invention is to provide a method for preparing a high-strength SAPO-34 microsphere catalyst prepared by spray drying a mixed slurry including a crystallized undried SAPO-34 slurry, a matrix, a binder, and an additive to prepare microspheres and firing the microspheres.

Further, an object of the present invention is to provide a high-strength SAPO-34 microsphere catalyst prepared by the preparation method.

In addition, an object of the present invention is to provide a method for preparing light olefins by using the high-strength SAPO-34 microsphere catalyst.

Advantageous Effects

The present invention may significantly improve the catalytic performance by using a mixed template to optimize the content of water or alcohol with a solvent in a SAPO-34 synthetic composition ratio and the stirring speed to readily prepare a SAPO-34 slurry having a crystal size of 1 or less, and may increase efficiency of the preparation process while reducing the cost by mixing the crystallized SAPO-34 slurry with a matrix, a binder, and an additive, without being dried and fired, to prepare a high-performance/high-strength microsphere-shaped catalyst. Further, a high-strength shaped catalyst may be prepared not only by adding an appropriate acid, but also without using a matrix, and the decrease in the reaction performance due to shaping of the catalyst may be minimized.

Best Mode

The method for preparing a SAPO-34 molecular sieve according to the present invention will be described in detail as follows.

The present invention relates to a method for preparing a high-strength SAPO-34 microsphere catalyst, including: spray drying a mixed slurry including a crystallized undried SAPO-34 slurry, a binder, and an additive to prepare microspheres; and firing the microspheres. Further, the mixed slurry may further contain a matrix.

The crystallized undried SAPO-34 slurry may be prepared by hydrothermally synthesizing a mixed synthetic gel in which a synthetic gel including an aluminum phosphate gel, a first organic template, and a solvent; and a silica-dissolving solution including a silica precursor, a second organic template, and a solvent are mixed.

When this is specifically described, first, an alumina precursor and phosphoric acid are mixed to prepare an aluminum phosphate gel, tetraethyl ammonium hydroxide or diethylamine as the first organic template is added thereto, an appropriate amount of water or alcohol as a solvent is added thereto, followed by stirring to prepare a synthetic gel. The alumina precursor is generally used in the art and is not particularly limited. However, specifically, aluminum alkoxide or pseudoboehmite may be used. Further, the temperature during stirring may be maintained in a range of 10 to 50° C. When the temperature is lower than 10° C., it is difficult to obtain a uniform dispersion and dissolution. When the temperature is higher than 50° C., the rate of gelation is so fast that dispersion may be difficult. Thus, it is preferable to maintain the above-described range.

Next, one or two or more silica precursors selected from diethylamine, morpholine, dipropylamine, isopropylamine, diethanolamine, triethylamine, cyclopentylamine, aminomethyl cyclohexane, piperidino, cyclohexylamine, tri-ethyl hydroxyethylamine, and pyridine, and more preferably one or two or more silica precursors selected from the group consisting of diethylamine, morpholine, dipropylamine, isopropylamine, diethanolamine, and triethylamine, as a second template, are added to water or alcohol as a solvent and stirred to dissolve silica, and then the silica-dissolving solution is mixed with the synthetic gel in Step 1. The silica precursor is generally used in the art and is not particularly limited. However, specifically, water glass, silica sol, fumed silica, and the like may be selected and used. The stirring and mixing is performed at 10 to 50° C. for 30 min to 5 hr. When the temperature is lower than 10° C., it is difficult to obtain a uniform gel. When the temperature is higher than 50° C., the synthetic gel already advances to a specific crystalline phase precursor. Thus, it is preferred that the above range be maintained.

In the present invention as described above, the amount of the total organic template including the first and second organic templates used in order to prepare a SAPO-34 catalyst may be maintained in a molar ratio of 1.0 to 4.0 based on 1 mole of the alumina precursor (based on $Al_2O_3$). In this case, when the amount of the organic template used is less than 1.0 molar ratio, it is difficult to obtain the SAPO-34 crystalline phase. When the amount is greater than 4.0 molar ratio, it may also be difficult to obtain the SAPO-34 crystalline phase and it is not preferred in terms of cost-effectively preparing the catalyst.

Further, the molar ratio of the first organic template and the second organic template is calculated as the molar ratio of the second organic template/the first organic template=0.3 to 3.0, and maintained preferably in the range of 0.5 to 2.0. In this case, when the amount used is less than 0.3 molar ratio or more than 3.0 molar ratio, it is not preferred because effects of the mixed template are deteriorated, the crystal size may be increased, and the costs for manufacturing the catalyst are increased.

In order to control the crystal size of SAPO-34 in the crystallized SAPO-34 slurry components that have not been dried, to 1 μm or less, the kind and content of the solvent is important, and the optimum solvents are different in kind and content according to the kind and composition of the organic templates. Accordingly, the contents of water and alcohol as a solvent were optimized in the present invention. The composition ratio of the solvent is appropriately in a molar ratio of 10 to 60 based on $Al_2O_3$, and more preferably in a molar ratio of 20 to 50. In this case, when the molar ratio of the solvent to the $Al_2O_3$ is less than 10, a problem with dispersion of the synthetic gel occurs. When the molar ratio is higher than 60, the crystal size is increased and the synthetic reactor is so large that the synthetic efficiency is decreased and the costs for preparing the catalyst is increased, which is disadvantageous.

Next, the mixed synthetic gel is put into an autoclave, matured while being stirred at 20 to 120° C. for 0 to 24 hr and preferably 0.5 to 24 hr, and stirred at 150 to 200° C. for 5 to 48 hr to prepare a crystallized SAPO-34 slurry including the organic template by a hydrothermal synthetic method for performing crystallization. When the maturing temperature is lower than 20° C., maturing effects of the synthetic gel are deteriorated. When the temperature is higher than 120° C., the above-described range should be maintained because the maturing step is completed and then crystallization begins. Further, when the crystallization temperature is lower than 150° C., the SAPO-34 molecular sieve grows slowly in crystal growth and may be produced in a phase where the amorphous portion and the crystalline SAPO-34 are mixed. When the temperature is higher than 200° C., the SAPO-34 crystal grows so great that the life-span of the catalyst is shortened when the SAPO-34 crystal is applied to the methanol-to-olefin (MTO) reaction.

Subsequently, the crystallized SAPO-34 slurry is mixed with a binder and an additive without being dried and fired, a high-strength microsphere-shaped catalyst is prepared by a spray drying method, and a matrix may be further added thereto to prepare a high-strength microsphere-shaped catalyst.

The binder serves as a glue between the matrix and the catalyst or between the catalyst and the catalyst. In the present invention, the binder may use one or more selected from alumina sol, silica sol, and poly aluminum chloride, and is used in an amount of preferably 50 to 300 parts by weight, and more preferably 80 to 280 parts by weight based on 100 parts by weight of the crystallized undried SAPO-34 slurry. In this case, when the binder is used in an amount of less than 50 parts by weight, the strength of the catalyst may be reduced. In contrast, when the binder is used in an amount of more than 300 parts by weight, the reaction activity of the catalyst may be deteriorated. Thus, it is preferable to use the binder within the range. Further, when an alumina sol is used as the binder, it is suitable to use a binder in which $Al_2O_3$ is present in an amount of 5 to 40 wt % based on the total weight of the alumina sol. When a silica sol is used, it is suitable to use a binder in which $SiO_2$ is present in an amount of 10 to 50 wt % based on the total weight of the silica sol.

The additive as an acid has effects on the reactivity of the methanol-to-olefin (MTO) reaction and catalyst strength, and thus the kind and content of an appropriate acid needs to be used. In the present invention, the additive may use one or two or more selected from hydrochloric acid, nitric acid, sulfuric acid, acetic acid, and formic acid, and the acid (based on 100% concentration) may be used in an amount of preferably 0.5 to 9 parts by weight and more preferably 0.5 to 7 parts by weight, based on 100 parts by weight of the crystallized undried SAPO-34 slurry (based on including the SAPO-34 in an amount of 40 wt % based on the total weight of the SAPO-34 slurry). In this case, when the additive is used in an amount of less than 0.5 part by weight, the strength of the catalyst may be reduced. In contrast, when the additive is used in an amount of more than 9 parts by weight, the life-span of the catalyst may be shortened. Thus, it is preferred that the above range be maintained.

The matrix serves as making the catalyst composition in the present invention dense to increase the attrition resistance and strength, and the present invention is characterized in that a high-strength catalyst may be prepared while a matrix is not used or is used in a small amount. Further, one or two or more selected from kaolin, bentonite, montmorillonite, china clay, and boehmite may be used as the matrix. In addition, when the matrix is used, it is suitable to use the matrix in an amount of 150 parts by weight or less based on 100 parts by weight of the crystallized undried SAPO-34 slurry (based on including the SAPO-34 in an amount of 40 wt % based on the total weight of the SAPO-34 slurry). In this case, when the matrix is used in an amount of more than 150 parts by weight, the reaction activity may be reduced. Thus, it is preferred that the above range be maintained. The matrix may be used by relatively controlling the amount used thereof according to the content of the SAPO-34 as a solid of the crystallized undried SAPO-34 slurry.

Next, the microsphere is fired in air atmosphere and at a temperature of 500 to 700° C. to prepare a SAPO-34 microsphere catalyst from which the organic template is removed. When the firing temperature is lower than 500° C., the temperature is so low that the organic amine may not be fired to be completely removed. Meanwhile, when the temperature is higher than 700° C., some of the SAPO-34 crystal structure may be collapsed. Thus, it is preferred that the firing temperature be maintained within the above range.

Further, the present invention is characterized by a method for preparing light olefins by performing a reaction of converting $C_1$ to $C_4$ oxygen-including compounds (oxygenates) into olefins under the SAPO-34 microsphere catalyst and in a circulating-fluidized bed reactor. In addition, the conditions of the conversion reaction are not particularly limited, but it is preferable to perform the reaction at 250 to 550° C., an atmospheric pressure of 0.5 to 10, and a flow rate of 0.1 to 50 $hr^{-1}$ WHSV (weight hourly space velocity).

Hereinafter, the present invention will be described in more detail with reference to Examples. However, the scope of the present invention is not limited to the following Examples.

EXAMPLE

Synthetic Example 1

While an aluminum phosphate gel, in which aluminum isopropoxide (98%, Aldrich), phosphoric acid (85%, Samchun Co., Ltd.), and water were mixed, was slowly added dropwise to a solution in which tetraethylammonium hydroxide (first organic template, TEAOH) and water were mixed for 2 hr, the mixture was sufficiently stirred at 20° C. to prepare a synthetic gel.

Separately, fumed silica (99.9%, Aldrich, silica precursor) and diethylamine (second organic template, DEA) were mixed with water at 20° C. and stirred for 2 hr to be completely dissolved, thereby preparing a silica-dissolving solution.

The silica-dissolving solution was mixed with the synthetic gel, followed by stirring for 2 hr to prepare a mixed synthetic gel. In this case, the composition of the mixed synthetic gel was controlled as in the following Table 1 so as to have a molar ratio of $Al_2O_3:P_2O_5:SiO_2$:the first organic template:the second organic template:the solvent=1:1:0.3:1:1:30. The mixed synthetic gel was put into an autoclave, matured at 120° C. for 10 hr while being stirred at 200 rpm or more, crystallized at 200° C. for 24 hr to perform a hydrothermal synthesis, and then filtered and washed by using a centrifuge to obtain a crystallized SAPO-34 slurry which had not been dried.

Synthetic Examples 2 to 6 and Comparative Synthetic Examples 1 to 4

Crystallized SAPO-34 slurries which had not been dried were prepared in the same manner as in Synthetic Example 1 except that the kinds and amounts used of the first organic template, the second organic template, and the solvent were changed to perform Synthetic Examples 2 to and Comparative Synthetic Examples 1 to 4 as in the following Table 1.

injected thereto while water is being added, and a microsphere was prepared by a spray drying method. Next, the microsphere was fired in air atmosphere at 600° C. to prepare a SAPO-34 microsphere catalyst.

TABLE 1

| Division | Composition (Molar ratio based on $Al_2O_3$) | | | | Solvent | | Average Crystal Size (μm) |
|---|---|---|---|---|---|---|---|
| | First Organic Template | | Second Organic Template | | | | |
| | Kind | Molar ratio (x) | Kind | Molar ratio (y) | Water (z) | Ethanol (z) | |
| Synthetic Example 1 | TEAOH[(1)] | 1 | DEA | 1 | 30 | — | <0.5 |
| Synthetic Example 2 | TEAOH | 1 | DEA | 1 | 50 | — | 0.7 |
| Comparative Synthetic Example 1 | TEAOH | 1 | DEA | 1 | 70 | — | 2.0 |
| Synthetic Example 3 | TEAOH | 1 | TEA[(3)] | 1 | 30 | — | <0.7 |
| Comparative Synthetic Example 2 | TEAOH | 1 | TEA | 1 | 70 | — | 2.0~3.0 |
| Synthetic Example 4 | DEA[(2)] | 2 | TEA | 1 | 30 | — | <1.0 |
| Synthetic Example 5 | DEA | 2 | DPA[(4)] | 1 | 30 | — | <1.0 |
| Synthetic Example 6 | DEA | 2 | DPA | 1 | 30 | 20 | <1.0 |

[(1)]TEAOH. Tetraethylammonium hydroxide
[(2)]DEA. Diethylamine
[(3)]TEA. Triethylamine
[(4)]DPA. Dipropylamine Example 1

The crystallized SAPO-34 slurry which had not been dried, prepared in Synthetic Example 1, a matrix, and a binder were quantitated and mixed to satisfy the weight ratio in the following Table 2, an acid was added thereto as an additive, followed by sufficiently stirring for 3 hr to prepare a mixed slurry. The content of the acid in the following Table is shown based on hydrochloric acid at 100% concentration.

The composition of the SAPO-34 catalyst shaping which had been performed in the present invention is shown in Table 2. The solid content of the formed slurry in which the crystallized SAPO-34 slurry which had not been dried, the matrix, the binder, and the additive were mixed was controlled to a concentration as high as possible in a range where a powder dryer does not clog when the slurry is Examples 2 to 11 and Comparative Examples 1 to 5

A mixed slurry was prepared by using the crystallized SAPO-34 slurry which had not been dried, prepared in Synthetic Example 1 in the same manner as in Example 1, except that the crystallized SAPO-34 slurry which had not been dried, the binder, the additive, and the matrix were used by varying the amounts thereof as in the following Table 2 to prepare a mixed slurry, and the mixed slurry was prepared in the form of a microsphere, and then Examples 2 to 11 and Comparative Examples 1 to 3 were performed by preparing a SAPO-34 microsphere catalyst. And then, in each of Comparative Examples 4 and 5, a dried SAPO-34 slurry was used to prepare a SAPO-34 microsphere catalyst instead of using the crystallized SAPO-34 slurry which had not been dried.

TABLE 2

| Division (Unit: Parts by weight) | SAPO-34 Slurry [(1)] | Dried SAPO-34 [(3)] | Matrix Kaolin [(2)] | Binder | | Additive | | pH of Mixed synthetic gel |
|---|---|---|---|---|---|---|---|---|
| | | | | Alumina Sol [(3)] | Silica sol [(4)] | Kind of Acid | Used amount [(5)] | |
| Example 1 | 100 | — | 67 | 267 | — | Hydrochloric Acid | 2.0 | 3.75 |
| Example 2 | 100 | — | 40 | 200 | — | Hydrochloric Acid | 1.5 | 4.08 |
| Example 3 | 100 | — | 24 | 160 | — | Hydrochloric Acid | 1.2 | 3.92 |
| Example 4 | 100 | — | 13.3 | 133 | — | Hydrochloric Acid | 1.0 | 4.02 |
| Example 5 | 100 | — | — | 100 | — | Hydrochloric Acid | 0.75 | 4.11 |
| Example 6 | 100 | — | 40 | 200 | — | Hydrochloric Acid | 3.0 | 3.85 |

TABLE 2-continued

| Division (Unit: Parts by weight) | SAPO-34 Slurry [1] | Dried SAPO-34 | Matrix Kaolin [2] | Binder Alumina Sol [3] | Silica sol [4] | Additive Kind of Acid | Used amount [5] | pH of Mixed synthetic gel |
|---|---|---|---|---|---|---|---|---|
| Example 7 | 100 | — | 40 | 200 | — | Hydrochloric Acid | 5.0 | 2.38 |
| Example 8 | 100 | — | 40 | 200 | — | Nitric acid | 1.5 | 4.21 |
| Example 9 | 100 | — | 40 | 200 | — | Acetic acid | 1.5 | 4.32 |
| Example 10 | 100 | — | 40 | 200 | — | Formic acid | 1.5 | 4.15 |
| Example 11 | 100 | — | 40 | — | 100 | Hydrochloric Acid | 1.5 | 6.13 |
| Comparative Example 1 | 100 | — | 40 | 200 | — | — | — | 4.90 |
| Comparative Example 2 | 100 | — | 40 | 200 | — | Phosphoric acid | 1.5 | 4.18 |
| Comparative Example 3 | 100 | — | 40 | 200 | — | Hydrochloric Acid | 10 | 1.91 |
| Comparative Example 4 | — | 100 [6] | 100 | 500 | — | — | — | 5.30 |
| Comparative Example 5 | — | 100 [6] | 100 | 500 | — | Hydrochloric Acid | 3.75 | 3.93 |

[1] SAPO-34 slurry: 40% by weight of SAPO-34
[2] Kaolin: Product from Samchun Pure Chemical Co., Ltd.
[3] Alumina sol: Richwood Trading Co., Ltd. AS-200, containg 10% by weight of $Al_2O_3$ based on the total weight of alumina sol
[4] Silica sol: Richwood Trading Co., Ltd. PS-M, containg 20% by weight of $SiO_2$ based on total weight of silica sol
[5] Based on acid concentration 100%
[6] SAPO-34 100% by weight.

Experimental Example 1: Physical Property Measurement Experiment

The SAPO-34 microsphere catalysts prepared in Examples 1 to 11 and Comparative Examples 1 to 5 were used to perform wear rate measurement experiments in accordance with the ASTM D5757-95 method, and the results thereof are shown in the following Table 3. Further, the content of phosphorus in the SAPO-34 microsphere catalyst was confirmed through ICP analysis to obtain the content of the SAPO-34 as an actual solid based thereon, and the content is shown in the following Table 3. In addition, the MTO reaction performances of shaped catalysts according to the kind and content of the acid added during the shaping were compared by using a ½-inch fixed bed reactor under conditions of a reaction temperature of 400° C., 10 volume % of the concentration of methanol diluted with nitrogen, and 1.6 $hr^{-1}$ weight hourly space velocity (WHSV) based on methanol.

TABLE 3

| | SAPO-34 Content [1] % by weight | Wear Rate (%) |
|---|---|---|
| Example 1 | 24.48 | 11.1 |
| Example 2 | 31.78 | 7.5 |
| Example 3 | 41.44 | 6.5 |
| Example 4 | 50.26 | 5.2 |
| Example 5 | 66.46 | 5.5 |
| Example 6 | 35.64 | 9.2 |
| Example 7 | 30.27 | 8.7 |
| Example 8 | 30.71 | 9.2 |
| Example 9 | 30.10 | 10.9 |
| Example 10 | 30.61 | 10.5 |
| Example 11 | 31.34 | 9.8 |
| Comparative Example 1 | 31.57 | 17.4 |
| Comparative Example 2 | Impossible to be measured | 11.8 |
| Comparative Example 3 | 29.08 | 9.4 |
| Comparative Example 4 | 33.26 | 27.2 |
| Comparative Example 5 | 32.84 | 18.3 |

[1] The content of SAPO-34 is expressed as % by weight based on the total weight of the SAPO-34 microsphere catalyst.

As shown in Table 3, it was confirmed that the SAPO-34 microsphere catalyst prepared by directly using the SAPO-34 slurry which had not been dried according to the present invention had been significantly improved in terms of strength of the catalysts, compared to Comparative Examples 4 and 5 in which the SAPO-34 slurry catalysts had been prepared by using the dried SAPO-34 slurry. In particular, in the case of Examples 1 to 4, it was confirmed that as the catalyst content was increased, the strength was increased. In the case of Example 5, it was confirmed that a high-strength shaped catalyst may be prepared even without using a matrix. It was confirmed that after the crystallization, a high-strength catalyst may be obtained by using the SAPO-34 slurry which had not been dried, or that a shaped catalyst having a high catalyst ratio may be prepared without using a matrix or by minimally using the matrix, and thus the decrease in the catalyst activity due to shaping of the catalyst may be minimized. Further, it is expected that after the SAPO-34 slurry is synthesized, the filtration and purification processes may be simplified and the drying and firing processes could be eliminated to reduce the preparation costs. In addition, in the case of Comparative Example 1 in which an acid was not used, it was confirmed that the strength thereof was low.

Experimental Example 2: Preparation of Olefins

The SAPO-34 microsphere catalysts in Example 2, Examples 6 to 11, and Comparative Examples 1 to 3 were used to perform light olefin synthesis reactions. The reactions were performed in a fixed bed reactor under reaction conditions of 400° C., normal pressure, and 1.6 hr$^{-1}$ weight hourly space velocity (WHSV), and the conversion rate and selectivity are shown in the following Table 4.

TABLE 4

| Sample | Reaction time 50 min | | | | Reaction time 210 min | | | |
|---|---|---|---|---|---|---|---|---|
| | Conversion rate (%) | Selectivity of light olefins (%) | | | Conversion rate (%) | Selectivity of light olefins (%) | | |
| | | $C_2$ | $C_3$ | $C_4$ | | $C_2$ | $C_3$ | $C_4$ |
| Example 2 | 98.5 | 43.7 | 37.0 | 8.3 | 88.6 | 42.8 | 35.4 | 5.5 |
| Example 5 | 99.6 | 46.5 | 38.2 | 5.6 | 96.4 | 45.3 | 36.8 | 5.2 |
| Example 6 | 98.0 | 43.6 | 38.1 | 7.1 | 89.1 | 40.2 | 33.2 | 3.8 |
| Example 7 | 96.1 | 44.3 | 37.0 | 6.8 | 84.5 | 39.9 | 32.7 | 4.7 |
| Example 8 | 98.0 | 47.6 | 37.1 | 5.0 | 85.4 | 43.8 | 32.0 | 3.8 |
| Example 9 | 94.3 | 48.6 | 33.3 | 4.4 | 83.3 | 39.4 | 31.4 | 4.0 |
| Example 10 | 99.2 | 43.0 | 42.0 | 6.2 | 95.9 | 48.0 | 39.8 | 4.1 |
| Example 11 | 94.5 | 44.2 | 37.3 | 5.6 | 82.1 | 41.8 | 32.6 | 3.5 |
| Comparative Example 1 | 99.4 | 43.9 | 41.8 | 5.5 | 84.4 | 43.3 | 36.4 | 3.1 |
| Comparative Example 2 | 68.4 | <10 | | | <50 | 0 | | |
| Comparative Example 3 | 92.3 | 40.5 | 34.2 | 4.8 | 67.6 | <10 | | |

As shown in Table 4, whether an acid was added to the shaped catalysts prepared in the present invention, the kind and content of the acid, and effects of the kind of liquid phase binder on the MTO reaction performance were observed. When the acid was used as an additive, it could be known that the MTO reaction performance was not deteriorated while the strength was significantly improved. In particular, in the case of using formic acid, the reaction performance was rather improved. However, in the case of Comparative Example 2 in which phosphoric acid was used, phosphorus caused to poison the reaction activity point of the catalyst thereby decreasing the activity.

The invention claimed is:

1. A method for preparing a SAPO-34 microsphere catalyst which is applied to a methanol-to-olefin (MTO) reaction, comprising:
spray drying a mixed slurry comprising 100 parts by weight of a crystallized undried silicoaluminophosphate-34 (SAPO-34) slurry, 50-300 parts by weight of a binder and 0.5-5 parts by weight of an additive to prepare microspheres; and
firing the microspheres, wherein the binder consists of one or more selected from an alumina sol and a silica sol, and wherein the additive consists of one or two or more selected from hydrochloric acid, nitric acid, acetic acid, and formic acid,
wherein the crystallized undried SAPO-34 slurry is prepared by hydrothermally synthesizing a mixed synthetic gel in which a synthetic gel comprising an aluminum phosphate gel, a first organic template and a solvent; and a silica-dissolving solution comprising a silica precursor, a second organic template and a solvent are mixed,
wherein the mixed slurry comprises kaolin as a matrix in range of 13.3-67 parts by weight based on 100 parts by weight of the SAPO-34 slurry,
wherein the solvent comprises one or two selected from water and alcohol in a molar ratio of 10 to 60 based on 1 mole of an alumina precursor (based on $Al_2O_3$),
wherein the crystallized undried SAPO-34 slurry includes SAPO-34 with average crystal size of less than 1 μm,
wherein the hydrothermal synthesis is performed by putting the mixed synthetic gel into an autoclave, maturing the mixed synthetic gel while being stirred at 20° C. to 120° C. for 0.5 hr to 24 hr and stirring the mixed synthetic gel at 150° C. to 200° C. for 5 hr to 48 hr to perform crystallization,
wherein a molar ratio calculated by the first organic template/the second organic template is 0.5 to 2.0,
wherein the SAPO-34 microsphere catalyst is used in circulating-fluidized bed reactor for preparing light olefins.

2. The method of claim 1, wherein the aluminum phosphate gel comprises water, an alumina precursor, and phosphoric acid; the first organic template comprises one or more selected from tetraethylammonium hydroxide and diethylamine; and the second organic template comprises one or two or more selected from morpholine, dipropylamine, isopropylamine, diethanolamine, triethylamine, diethylamine, cyclopentylamine, aminomethyl cyclohexane, piperidine, cyclohexylamine, tri-ethyl hydroxyethylamine, and pyridine.

3. The method of claim 1, wherein the firing is performed at a temperature of 500 to 700° C.

4. The method of claim 1, wherein the additive is formic acid.

5. The method of claim 1, wherein the crystallized undried silicoaluminophosphate-34 (SAPO-34) slurry includes 40 wt % of SAPO-34.

6. A SAPO-34 microsphere catalyst prepared by the method of any one selected from claims 1, 2, and 3.

7. A method for preparing a SAPO-34 microsphere catalyst which is applied to a methanol-to-olefin (MTO) reaction, comprising:
spray drying a mixed slurry comprising 100 parts by weight of a crystallized undried silicoaluminophosphate-34 (SAPO-34) slurry, 50-300 parts by weight of a binder and 0.5-5 parts by weight of an additive to prepare microspheres; and
firing the microspheres at a temperature of 500 to 700° C., wherein the binder consists of one or more selected from an alumina sol and a silica sol, and wherein the additive comprises formic acid,
wherein the crystallized undried SAPO-34 slurry is prepared by hydrothermally synthesizing a mixed synthetic gel in which a synthetic gel comprising an aluminum phosphate gel, a first organic template and a solvent; and a silica-dissolving solution comprising a silica precursor, a second organic template and a solvent are mixed, wherein the mixed slurry comprises kaolin as a matrix in range of 13.3-67 parts by weight based on 100 parts of the SAPO-34 slurry, wherein the solvent comprises one or two selected from water and alcohol in a molar ratio of 10 to 60 based on 1 mole of an alumina precursor (based on $Al_2O_3$), wherein the hydrothermal synthesis is performed by putting the mixed synthetic gel into an autoclave, maturing the mixed synthetic gel while being stirred at 20 to 120° C. for 0.5 to 24 hr, and stirring the mixed synthetic gel at 150 to 200° C. for 5 to 48 hr to perform crystallization, and wherein the crystallized undried silicoaluminophosphate-34 (SAPO-34) slurry includes 40 wt % of SAPO-34, wherein the crystallized undried SAPO-34 slurry includes SAPO-34 with average crystal size of less than 1 μm, wherein the hydrothermal synthesis is performed by putting the mixed synthetic gel into an autoclave, maturing the mixed synthetic gel while being stirred at 20° C. to 120° C. for 0.5 hr to 24 hr and stirring the mixed synthetic gel at 150° C. to 200° C. for 5 hr to 48 hr to perform crystallization, wherein a molar ratio calculated by the first organic template/the second organic template is 0.5 to 2.0, wherein the SAPO-34 microsphere catalyst is used in circulating-fluidized bed reactor for preparing light olefins.

8. A method for preparing a silicoaluminophosphate (SAPO) microsphere catalyst, the method comprising:

mixing together an aluminum precursor, phosphoric acid, water and a first organic template to prepare a synthetic gel;

dissolving a silica precursor into second organic template to prepare a silica-dissolved solution;

stirring together the silica-dissolved solution with the synthetic gel to prepare a mixed synthetic gel;

autoclaving the mixed synthetic gel at a between 150° C. to 200° C. to obtain a crystallized SAPO slurry;

spray drying a mixture of the SAPO slurry, a binder, an additive, and a matrix to prepare a spray dried product; and firing the spray dried product to prepare the SAPO microsphere catalyst, wherein the spray drying a mixed slurry comprising 100 parts by weight of the SAPO slurry, 50-300 parts by weight of the binder, 13.3-67 parts by weight of the matrix and 0.5-5 parts by weight of the additive, wherein the SAPO microsphere catalyst is used in circulating-fluidized bed reactor for preparing light olefins.

9. The method of claim 8 wherein the alumina precursor is selected from the group consisting of aluminum alkoxide, pseudoboehmite, and aluminum isopropoxide.

10. The method of claim 8, wherein the first organic template is selected from the group consisting of tetraethylammonium hydroxide and diethylamine.

11. The method of claim 8, wherein the second organic template is selected from the group consisting of morpholine, dipropylamine, isopropylamine, diethanolamine, triethylamine, diethylamine, cyclopentylamine, aminomethyl cyclohexane, piperidine, cyclohexylamine, tri-ethyl hydroxyethylamine, and pyridine.

12. The method of claim 8, wherein the silica precursor is selected from the group consisting of water glass, silica sol, and fumed silica.

13. The method of claim 8, wherein the binder is selected from the group consisting of an alumina sol, a silica sol, and poly aluminum chloride.

14. The method of claim 8, wherein the additive is selected from the group consisting of hydrochloric acid, nitric acid, sulfuric acid, acetic acid, and formic acid.

15. The method of claim 8, wherein the matrix is selected from the group consisting of kaolin, bentonite, montmorillonite, china clay, and boehmite.

16. The method of claim 8, wherein the firing is performed between 500° C. and 700° C.

* * * * *